United States Patent [19]

Uchino et al.

[11] Patent Number: 5,229,038

[45] Date of Patent: Jul. 20, 1993

[54] ORGANIC NONLINEAR OPTICAL MATERIAL AND METHOD OF CONVERTING THE WAVELENGTH OF LIGHT USING SAID MATERIAL

[75] Inventors: Nobuhiko Uchino; Masaki Okazaki; Koji Matsuo; Yoji Okazaki, all of Kanagawa, Japan

[73] Assignee: Fuji Photo Film Co., Ltd., Kanagawa, Japan

[21] Appl. No.: 757,356

[22] Filed: Sep. 10, 1991

[30] Foreign Application Priority Data

Sep. 12, 1990 [JP] Japan ................................. 2-242218

[51] Int. Cl.$^5$ .......................... F21V 9/00; F21V 9/04; G02B 6/00; C07C 241/00
[52] U.S. Cl. ................................ 252/582; 252/587; 252/589; 359/328; 564/148; 564/149; 564/150
[58] Field of Search ...................... 252/582, 587, 589; 564/148, 149, 150; 359/328

[56] References Cited

U.S. PATENT DOCUMENTS

| | | | |
|---|---|---|---|
| 3,162,680 | 12/1964 | Biel | 564/150 |
| 3,177,251 | 5/1965 | Carron et al. | 564/150 |
| 4,233,209 | 11/1980 | Dexter et al. | 564/150 |
| 4,334,015 | 6/1982 | Yarian | 564/149 |

FOREIGN PATENT DOCUMENTS 532468 10/1956 Canada ................................. 564/149

OTHER PUBLICATIONS

Chemical Abstracts 110:510f, (Ponka et al.), 1989.

*Primary Examiner*—Robert L. Stoll
*Assistant Examiner*—Philip Tucker
*Attorney, Agent, or Firm*—Sughrue, Mion, Zinn, Macpeak & Seas

[57] ABSTRACT

A nonlinear optical material comprising a compound represented by the following general formula (I):

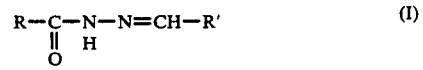

wherein R and R' are each an alkyl group, an aryl group, an aralkyl group or a hetero ring, and a method of converting the wavelength of laser light using the organic nonlinear optical material.

5 Claims, 1 Drawing Sheet

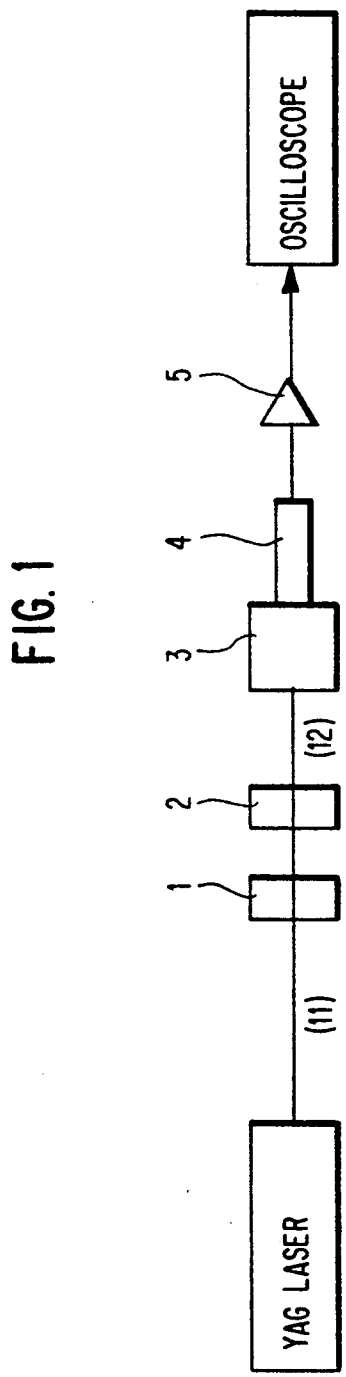

ORGANIC NONLINEAR OPTICAL MATERIAL AND METHOD OF CONVERTING THE WAVELENGTH OF LIGHT USING SAID MATERIAL

FIELD OF THE INVENTION

This invention relates to a nonlinear optical material suitable for use in wavelength converters and various other devices that utilize nonlinear optical effects. The invention also relates to a method of converting the wavelength of light using said nonlinear optical material.

BACKGROUND OF THE INVENTION

Nonlinear optical materials which produce nonlinearity between polarization and electric field upon application of a strong optoelectric field as by laser light are drawing the attention of researchers. Details of such nonlinear optical materials are given in many references including: "Nonlinear Optical Properties of Organic and Polymeric Materials", ACS SYMPOSIUM SERIES 233, ed. by David J. Williams, American Chemical Society, 1983; "Yuki Hisenkei Kogaku Zairyo (Organic Nonlinear Optical Materials)", ed. by M. Kato and H. Nakanishi, CMC, 1985; and "Nonlinear Optical Properties of Organic Molecules and Crystals", Vols. 1 and 2, ed. by D. S. Chemla and J. Zyss, Academic Press, 1987.

One application of nonlinear optical materials is in wavelength converting devices that use not only the second harmonic generation (SHG) based on quadratic (second-order) nonlinear effects but also sum and difference frequencies. The only commercially used nonlinear optical materials have been inorganic perovskites typified by lithium niobate. However, it has recently become clear that $\pi$-electron conjugated organic compounds having both an electron donating group and an electron withdrawing group have much better performance as nonlinear optical materials than the aforementioned inorganic materials.

In order to form nonlinear optical materials having better performance, compounds having high nonlinear susceptibilities in a molecular state must be arranged in such a way that inverse symmetry will not occur. For the development of high nonlinear susceptibility, compounds having long $\pi$-electron conjugate chains are known to be useful and described in the references mentioned above. However, the absorption maxima of those compounds are shifted to the longer wavelength and the transmittance of certain light, say, blue light will decrease to impede the generation of blue light as a second harmonic wave. This problem also occurs in p-nitroaniline derivatives. The significant effect of light transmittance on the efficiency of second harmonic generation is obvious from FIG. 4 on page 186 of Alain Azéma, Proceedings of SPIE, Vol. 400, New Optical Materials, 1983.

It is therefore desired to develop a nonlinear optical material having high transparency to blue light. Attempts have heretofore been made to replace carbon atoms on the benzene nucleus of nitroaniline by other atoms such as nitrogen atoms but no completely satisfactory results have been attained.

More effective methods have been proposed in JP-A-62-210430 and JP-A-62-210432. The term "JP-A" used herein refers to a published unexamined patent application, and the term "JP-B" refers to a published examined patent application.

Many nonlinear optical materials are described in JP-A-62-59934, JP-A-63-23136, JP-A-63-26638, JP-B-63-31768, JP-A-63-163827, JP-A-63-146025, JP-A-63-85526, JP-A-63-239427, JP-A-1-100521, JP-A-64-56425, JP-A-1-102529, JP-A-1-102530, JP-A-1-237625 and JP-A-1-207724.

As already mentioned before, high nonlinear susceptibility in a molecular state is not the sole condition for compounds to be useful as quadratic nonlinear optical materials and it is also essential that the arrangement of molecules in an aggregated state have no inverse symmetry. However, it is extremely difficult in the state of the art to predict the molecular arrangement of compounds and, in addition, the probability of occurrence of suitable compounds among all organic compounds is not high.

SUMMARY OF THE INVENTION

The present invention has been achieved under these circumstances and has as an object providing an organic nonlinear optical material that exhibits high nonlinear response and that is capable of high transmission of blue light.

Another object of the present invention is to provide a method that utilizes the nonlinear response of said material which is particularly related to the conversion of light wavelength.

As a result of the intensive studies conducted by the present inventors, it has been found that the objects of the present invention can be attained by using compounds of the following general formula (I) as organic nonlinear optical responsive compounds:

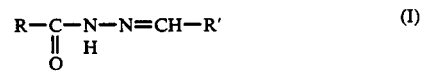

(wherein R and R' each represents an alkyl group, an aryl group, an aralkyl group or a hetero ring).

BRIEF DESCRIPTION OF THE DRAWING

FIG. 1 is a schematic diagram of an apparatus for measuring second harmonic generation by a powder method.

DETAILED DESCRIPTION OF THE INVENTION

The groups denoted by R and R' are each an alkyl group, an aryl (straight chain or branched) group, an aralkyl group or a hetero ring which may be substituted. The preferred alkyl group has 1-8 carbon atoms and may be examplified by methyl, ethyl, propyl, isopropyl and t-butyl. The preferred aryl group has 6-18 carbon atoms and may be exemplified by phenyl, tolyl, 4-methoxyphenyl, 4-amino-phenyl, 4-diethylaminophenyl, 4-hydroxyphenyl, 4-methylthiophenyl, 4-mercaptophenyl, 4-phenoxyphenyl, 4-phenylthiophenyl, 4-nitrophenyl, 4-cyanophenyl, 4-trifluoromethylphenyl, 4-acetylphenyl, 4-carboxylphenyl, 4-ethoxycarbonylphenyl, 4-fluorophenyl, 4-chlorophenyl, 4-bromophenyl and 4-iodophenyl. The preferred aralkyl group has 7-19 carbon atoms and may be exemplified by benzyl, phenethyl, p-methylbenzyl and p-methylphenetyl. The hetero ring means a hetero ring which includes a 6-member ring structure containing at least one nitrogen atom. Exemplary hetero rings include a pyridine ring, a pyrimidine ring, a pyradine ring, a quinoline ring, a 4-methylpyridine ring and a 4-methylquinoline ring. In order to increase the quadratic nonlinear optical constant ($\beta$) in a molecular state, R is preferably an aryl group having an electron donating group, with a 4-hydroxyphenyl group being particularly preferred, and R' is preferably a hetero ring or an aryl group having an electron withdrawing group, with a pyridine ring and a 4-nitrophenyl group being particularly preferred.

The term "electron withdrawing group" as used hereinabove refers to a substituent having a positive substituent constant $\sigma_p$, whereas the term "electron donating group" refers to a substituent having a negative substituent constant $\sigma_p$.

The specific values of substituent constant $\sigma_p$ are listed in "Structural Activity Correlations of Drugs—Guidelines for Drug Design and Studies of the Mechanism of Action" in Special Issue No. 122 of "Kagaku no Ryoiki (Area of Chemistry)", compiled by the Commission of Structural Activity Correlations, pp. 95–111, Nankodo, and Corwi Hansch and Albert Leo, "Substituent Constants for Correlation Analysis in Chemistry and Biology", pp. 69–161, John Wiley & Sons.

Specific examples of the compounds that can be used in the present invention are listed below but it should be understood that the present invention is by no means limited to those examples.

Compound 1

Compound 2

Compound 3

Compound 4

Compound 5

Compound 6

Compound 7

-continued

Compound 8
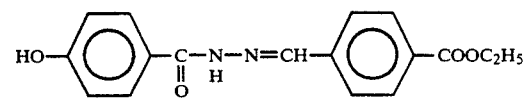

Compound 9
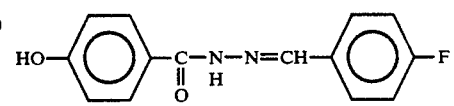

Compound 10
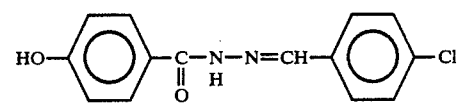

Compound 11
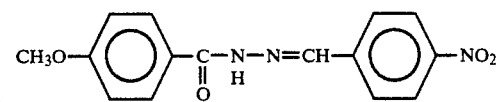

Compound 12
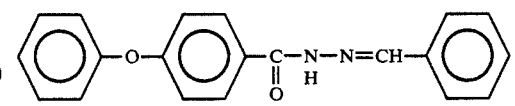

Compound 13
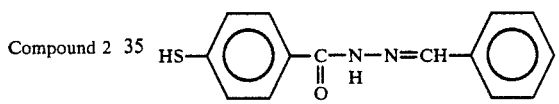

Compound 14
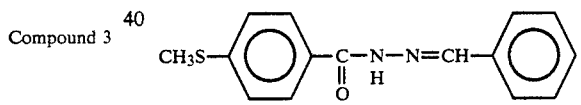

Compound 15
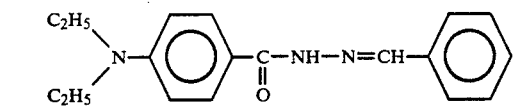

Compound 16
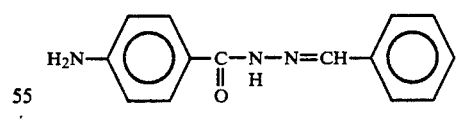

Compound 17
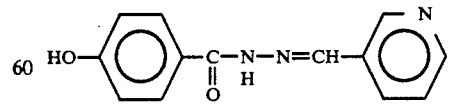

Compound 18
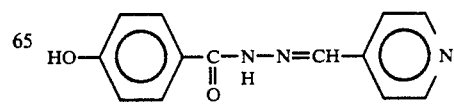

-continued

Compound 19

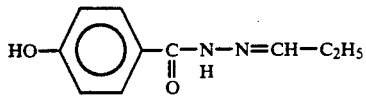

Compound 20

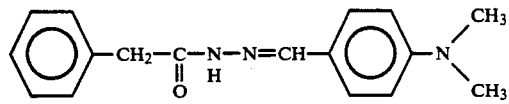

These compounds can be synthesized in accordance with the following scheme 1:

Scheme 1

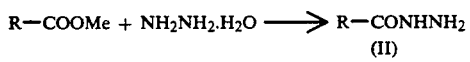

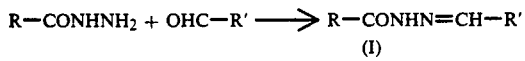

Specific examples of the synthesis of Compounds 1 and 3 are shown below and the other compounds can be synthesized in basically the same manner.

Synthesis Example 1 (Synthesis of Compound 1)

(i) Synthesis of (II)

A mixture of methyl benzoate (13.6 g, or 0.1 mol) and hydrazine monohydrate (5 g, or 0.1 mol) was refluxed in ethanol (100 ml) for 3 h. After the end of the reaction, the mixture was cooled to room temperature and the resulting crystal was recovered by filtration and recrystallized with ethanol to obtain a compound of the general formula (II). Yield, 13.2 g (97%)

(ii) Synthesis of compound 1

A mixture of (II) (6.8 g, or 0.05 mol and benzaldehyde (5.3 g, or 0.05 mol) was refluxed in ethanol (100 ml) for 2 h. After the end of the reaction, the mixture was cooled to room temperature and the resulting crystals were recovered by filtration and recrystallized with ethanol to obtain compound 1. The NMR and IR spectra of this compound were in agreement with those of the end compound. The values found in elemental analysis of C, H and N for the empirical formula were also in agreement with the calculated values. Yield, 11.2 g (100%); m.p. 203°-204° C.

Synthesis Example 2 (Synthesis of Compound 3)

(i) Synthesis of (II)

A mixture of methyl p-hydroxybenzoate (15.2 g, or 0.1 mol) and hydrazine monohydrate (5 g, or 0.1 mol) was refluxed in ethanol (100 ml) for 5 h. After the end of the reaction, the mixture was cooled to room temperature and the resulting crystal was recovered by filtration and recrystallized with ethanol to obtain a compound of the general formula (II). Yield, 12.8 g (84%).

(ii) Synthesis of compound 3

A mixture of (II) (7.6 g, or 0.05 mol) and benzaldehyde (5.3 g, or 0.05 mol) was heated under reflux in ethanol (100 ml) for 1 h. After the end of the reaction, the mixture was cooled to room temperature and the resulting crystal was recovered by filtration and recrystallized with ethanol to obtain a compound 3. The NMR and IR spectra of this compound were in agreement with those of the end compound. The values found in elemental analysis of C, H and N for the empirical formula were also in agreement with the calculated values. Yield, 8.9 g (74%); m.p. 221°-222° C.

As will be apparent from the example that is shown later in this specification, the nonlinear optical material of the present invention is particularly useful as a material for converting the wavelength of laser light. It should, however, be noted that the use of the nonlinear optical material of the present invention is by no means limited to wavelength converting devices and it can be applied to any devices that utilize the nonlinear optical effect. Other devices than wavelength converters with which the nonlinear optical material of the present invention can be used include optical bistable devices (e.g. optical memory devices, light pulse waveform control devices, photolimiters, differential amplifiers, phototransistors, A/D converters, optical logic devices, photomultivibrators and optical flip-flop circuits), optical modulators and phase conjugated optical devices.

The compounds of the general formula (I) can be used as nonlinear optical materials in various forms including powder, molecular inclusions within host lattices (e.g. polymers, clathrates compounds, solid solutions and liquid crystals), thin layers deposited on substrates (e.g. Langmuir-Blodgett membrane), single crystals and solutions.

The compounds can also be used as pendants in polymers, polydiacetylene, etc.

For details of these methods, see "Nonlinear Optical Properties or Organic and Polymeric Materials", ed. by D. J. Williams, supra, and other references.

Examples of the laser light sources that can be used as fundamental waves are listed in Table 1. The wavelengths of fundamental waves are in no way limited except by the effect of materials absorption. This is clear from Laser & Optronics, p. 59, November 1987.

TABLE 1

| | Operating Wavelengths and Other Characteristics of Lasers | | | | | |
|---|---|---|---|---|---|---|
| | Operating wavelength, $\mu$m | | | | | Operating condition (pulse or CW), peak power, |
| Laser | 0.8 | 1.0 | 1.2 | 1.4 | 1.6 | mode of propagation |
| Semiconductor laser | | | | | | |
| GaInAsP/In laser | | | ⊢―――⊣ | | | CW Pmax = 200 mW (single mode) |
| GaAlAs/GaAs laser | ⊢――⊣ | | | | | CW Pmax = 150 mW (single mode) CW Pmax = 3 W (multimode) |

TABLE 1-continued

Operating Wavelengths and Other Characteristics of Lasers

| Laser | Operating wavelength, μm (0.8 – 1.6) | Operating condition (pulse or CW), peak power, mode of propagation |
|---|---|---|
| InGaAs/GaAs laser | 0.8–1.0 | CW Pmax = 150 mW (single mode) <br> CW Pmax = 3 W (multimode) |
| Solid laser | | |
| Nd:YAG laser | 0.946  1.064  1.32 | CW Pmax = 5 W (single mode) <br> Q-switch pulse Pmax = <10 MW |
| Ti:Al$_2$O$_3$ laser | 0.8–1.1 | CW Pmax = 5 W (single mode) |
| Others | | |
| Dye laser | ←–––| |

The following example is provided for the purpose of further illustrating the present invention but is in no way to be taken as limiting.

EXAMPLE

Second harmonic generation from the powders of compounds within the scope of the present invention was measured in accordance with the method described in S. K. Kurtz and T. T. Perry, "Journal of Applied Physics", Vol. 39, 3798, 1968. With pulsive YAG laser light ($\lambda = 1.064$ μm; beam diameter ≃ 1 mm; peak power ≃ 10 MW cm$^2$) being used as a fundamental wave, the intensity of the second harmonic wave generated from each sample was measured with the apparatus shown in FIG. 1. The apparatus containing the powder sample 1 consisted of a filter 2 for cutting off the fundamental wave, a spectrograph 3, a photomultiplier tube 4, and an amplifier 5. The light in optical path 11 had a wavelength of 1.064 μm and the light in optical path 12 had a wavelength of 0.532 μm. The measured intensity was compared with the intensity of second harmonic wave generated from urea. In case of low intensities, visual observations were conducted. In order to distinguish light emission due to the two-photon absorption of the fundamental wave (in particular, the emission of yellow and red light) from the second harmonic generation, the spectrograph was inserted to insure that only the second harmonic wave could be measured. The main objective of measurement by the powder method is to check for the nonlinearity of a test compound and its relative intensity should be taken as a reference value for the magnitude of its nonlinear effect.

The results of measurements are shown in Table 2.

TABLE 2

| Compound | SHG efficiency | EtOH λ max/nm | EtOH λ cut off/nm |
|---|---|---|---|
| 1 (Invention) | 4 | 299 | 351 |
| 3 (Invention) | 10 | 304 | 352 |
| 17 (Invention) | 8 | 304 | 340 |
| POM (Comparison) | 16 | 324 | 408 |
| MNA (Comparison) | 22 | 374 | 458 |
| NEPH (Comparison) | 3 | 410 | — |
| NFS (Comparison) | 30 | 375 | — |

* EtOH
λ cut off means the wavelength for 95% transmission in an ethanol solution at a concentration of $4 \times 10^{-4}$ mol/l.

It is clear from Table 2 that compounds 1, 3 and 17 within the scope of the present invention are capable of extremely high transmission of blue light.

The comparative compounds had the following structures:

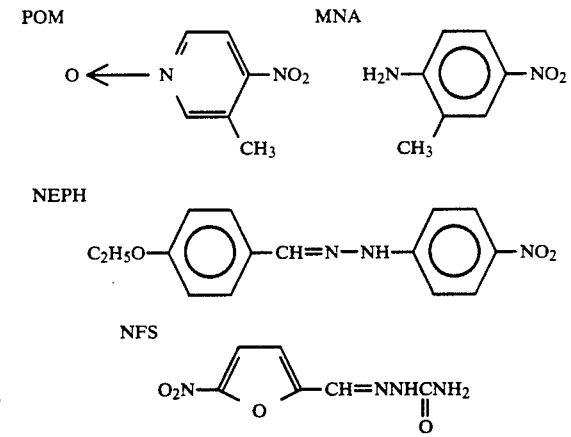

The compounds of the general formula (I) which showed SHG activity in measurements by the powder method can be used in wavelength converting devices that are fabricated by the following techniques as disclosed, for example, in U.S. Pat. No. 4,909,595.

1. A single crystal of the compound is formed in the core of an optical fiber, which is clad with glass to fabricate a wavelength converting device. When YAG laser light is admitted into the device, its second harmonic wave can be generated. Alternatively, a wavelength converting device of waveguide type can be constructed in a similar way to achieve second harmonic generation. Phase matching in this case is accomplished by the Cherenkov radiation. Another method that can be used is guided-wave phase matching. Wavelength conversion that can be achieved is by no means limited to conversion to the second harmonic wave and conversion to the third harmonic wave as well as the generation of sum and differential frequencies can also be accomplished.

2. In another method, a single crystal of the compound is formed and a slice is cut out of the bulk single crystal. When YAG laser light is admitted into the slice, its second harmonic wave can be generated. In this case, angular phase matching is adopted. The bulk single crystal need not be used outside the laser cavity; if desired, it may be used within the cavity of a solid laser such as an LD excited solid laser and this contributes to an enhanced efficiency of wavelength conversion. The same object can be achieved by mounting the single crystal within the external resonator of an LD.

Single crystals of the compounds can be formed by various growth techniques including the Bridgman method and the solvent evaporation method.

As already mentioned, wavelength conversion that can be achieved is not limited to conversion to the second harmonic wave and conversion to the third harmonic wave and even the generation of sum and differential frequencies can also be accomplished.

Furthermore, as a reference, U.S. Pat. No. 5,030,851 discussed physics of nonlinear optical crystals, processes and devices and the 1987 article by Barzoukas et al in J. Opt. Soc. Am. B. discusses nonlinear properties of organic molecules, such as SHG, frequency mixing, electroopic modulation, optic parametric emission, amplification and oscillation on general, and NPP and NPAN in particular.

Embodiments of wavelength converters of the present invention are surmmarized below:

(a) a nonlinear optical device comprising a crystal having nonlinear optical properties, and means for directing at least one incident beam of electromagnetic radiation into said crystal, whereby electromagnetic radiation emerging from said crystal contains at least one frequency different from the frequency of any incident beam of radiation, said crystal being a single crystal having the formula (I).

(b) a laser-diode-pumped solid-state laser comprising:
  i) a solid-state laser rod doped with a rareearth material;
  ii) a semiconductor laser for emitting a laser beam to pump said solid-state laser rod to oscillate a beam; and
  iii) a resonator including a bulk single crystal of an organic nonlinear optical material for converting the wavelength of the beam which is oscillated by said solid-state laser rod and the wavelength of the laser beam which is emitted by said semiconductor laser into the wavelength of a sum-frequency wave whose frequency is the sum of the frequencies of the oscillated beam and the laser beam, wherein said organic nonlinear optical material is represented by the formula (I).

(c) an electro-optic modulator comprising means for directing a beam of polarized radiation into a birefringent crystal, and means for applying an electric field to said crystal to change birefringence, whereby the polarization of radiation emerging from said crystal is changed, wherein said birefringent crystal has the formula (I).

(d) a Q-switched laser with Nd:YAG as gain medium having provided as an intracavity second harmonic generator a single crystal having the formula (I).

(e) a high efficiency, diode pumped compact laser comprising:
  a neodymium-YAG laser rod having a front end and a back end;
  a housing including means for holding the neodymium-YAG laser rod in fixed position in the housing with its front end forward;
  a laser diode for pumping the neodymium-YAG laser rod, having an output frequency sufficiently matched to the rod to pump the rod, secured in the housing behind and in optical alignment with the rod;
  output coupler means including a mirrored surface forming a front end of a laser cavity;
  rear mirror means forming a back end of the laser cavity, with the neodymium-YAG rod within the cavity;
  an intracavity frequency doubler within the laser cavity, positioned to receive the output beam of the laser rod and to halve its wavelength, doubling its frequency; and
  polarization control means for adjusting and maintaining the polarization of the laser beam to a polarization which optimizes frequency doubling of the laser beam by the frequency doubler, wherein said intracavity frequency doubler is a single crystal having the formula (I).

While the invention has been described in detail and with reference to specific embodiments thereof, it will be apparent to one skilled in the art that various changes and modifications can be made therein without departing from the spirit and scope thereof.

What is claimed is:

1. A nonlinear optical material comprising a compound represented by the following general formula (I):

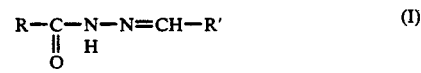

wherein R is a 1-8 carbon atom alkyl group or an electron donating 6-18 carbon atom aryl group substituted at the 4-position by a substituent selected from the group consisting of methoxy, amino, diethylamino, hydroxy, methylthio, mercapto, phenoxy, and phenylthio, and R' is a 1-8 carbon atom alkyl group, an electron withdrawing 6-18 carbon atom aryl group substituted at the 4-position by a substituent selected from the group consisting of nitro, cyano, trifluoromethyl, acetyl, carboxy, ethoxycarbonyl, fluorine, chlorine, bromine, and iodine, a 7-19 carbon atom aralkyl group or a six-membered heterocyclic ring containing at least one nitrogen atom.

2. A nonlinear optical material as in claim 1, wherein R is said electron donating 6-18 carbon atom aryl group.

3. A nonlinear optical material as in claim 1, wherein R' is said electron withdrawing 6-18 carbon atom aryl group or said six-membered heterocyclic ring.

4. A nonlinear optical material as in claim 1, wherein said heterocyclic ring is selected from the group consisting of pyridine, pyrimidine, pyrazine, and 4-methyl-pyridine.

5. A nonlinear optical material as in claim 1, wherein R is said aryl group and R' is said aryl group or said heterocyclic ring.

* * * * *